(12) United States Patent
Abergas et al.

(10) Patent No.: US 11,857,056 B2
(45) Date of Patent: Jan. 2, 2024

(54) DISPENSING PACKAGE AND METHOD FOR CONTROLLED DELIVERY OF A VISCOUS COMPOSITION

(71) Applicant: The Procter & Gamble Company, Cincinnati, OH (US)

(72) Inventors: Billy Gonzales Abergas, Singapore (SG); Mariane Ballerini Fernandes, Egham (GB); Vinayak Masanaiah, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 72 days.

(21) Appl. No.: 17/463,640

(22) Filed: Sep. 1, 2021

(65) Prior Publication Data

US 2022/0061498 A1 Mar. 3, 2022

Related U.S. Application Data (60) Provisional application No. 63/072,946, filed on Sep. 1, 2020.

(51) Int. Cl.
*A45D 40/04* (2006.01)
*A61K 9/06* (2006.01)

(52) U.S. Cl.
CPC ............... *A45D 40/04* (2013.01); *A61K 9/06* (2013.01); *A45D 2200/05* (2013.01); *A45D 2200/055* (2013.01); *A45D 2200/10* (2013.01)

(58) Field of Classification Search
CPC .... A45D 40/04; A45D 2200/05; A45D 40/26; A45D 40/06; A45D 2200/055;
(Continued)

(56) References Cited

U.S. PATENT DOCUMENTS

| | | | | |
|---|---|---|---|---|
| 2,085,446 A | * | 6/1937 | Philippe | A45D 40/0075 401/265 |
| 3,088,470 A | * | 5/1963 | Hall | A45D 40/26 401/266 |

(Continued)

FOREIGN PATENT DOCUMENTS

| | | |
|---|---|---|
| JP | 5412106 B2 | 2/2014 |
| JP | D1559629 | 9/2016 |

(Continued)

OTHER PUBLICATIONS

PCT Search Report and Written Opinion for PCT/US2021/045142 dated Jun. 21, 2023, 13 pages.

*Primary Examiner* — David J Walczak
(74) *Attorney, Agent, or Firm* — Gregory S. Darley-Emerson (57) ABSTRACT

Dispensing package for controlled delivery of a viscous composition on a target surface, the package having a dispensing head with a front surface having a front surface centroid and an opposing rear surface having a rear surface centroid, and a plurality of dispensing orifices extending therethrough, the dispensing orifices including a front open end having a front centroid on the front surface, a rear open end having a back centroid on the rear surface, and a dispensing orifice axis extending through the front and back centroids. A first dispensing orifice of the plurality of dispensing orifices has a first dispensing orifice axis inclined at a first orifice acute angle α1 (degrees) relative to the a plane extending along a center axis, so as to intersect the plane at a first point above the front surface.

21 Claims, 6 Drawing Sheets

(58) Field of Classification Search
CPC ........ A45D 2200/10; A61K 9/06; A61K 9/08;
A61K 9/107; B65D 83/0005; B65D
83/0011; B65D 83/0022
USPC ........................................ 401/9–12, 261–266
See application file for complete search history.

(56) References Cited

U.S. PATENT DOCUMENTS

| | | | |
|---|---|---|---|
| 5,000,356 | A | 3/1991 | Johnson et al. |
| 5,209,376 | A | 5/1993 | Dirksing |
| 6,533,195 | B2 | 3/2003 | Sinders |
| 6,932,530 | B1 * | 8/2005 | Bissel ................ B65D 83/0011 401/175 |
| 8,550,381 | B2 | 10/2013 | Burmester et al. |
| 9,795,205 | B2 | 10/2017 | Bolander et al. |
| 2008/0166174 | A1 | 7/2008 | Kennedy et al. |
| 2011/0150557 | A1 | 6/2011 | Bissah et al. |
| 2020/0139385 | A1 | 5/2020 | Hartranft et al. |

FOREIGN PATENT DOCUMENTS

| | | |
|---|---|---|
| KR | 20120017354 A | 2/2012 |
| KR | 20200020599 A | 2/2020 |
| TW | 201726260 A | 8/2017 |
| WO | 2016084955 A1 | 6/2016 |

* cited by examiner

DISPENSING PACKAGE AND METHOD FOR CONTROLLED DELIVERY OF A VISCOUS COMPOSITION

FIELD OF THE INVENTION

The present invention relates to a dispensing package and a method for controlled delivery of a viscous composition on a target surface.

BACKGROUND OF THE INVENTION

Viscous compositions such as cosmetic creams or therapeutic ointments are known to be distributed in a package made up of a jar containing the cream or ointment, wherein the jar is covered with a lid. As convenient and portable as these packages are, they still remain potentially unsanitary. For example, the consumer touches the ointment in the jar with his or her fingers before applying it to the skin on the arm or any part of the body. This contact with the hand can create mess for some consumers and can give concerns linked to contamination in the ointment remaining in the jar. Further, for some consumers, it is difficult to control or determine an amount of ointment being applied. Further, the ointment tends to adhere to the user's hand(s) after application to the skin thereby requiring washing or wiping to remove it from the hand after use.

To address the abovementioned sanitary concerns, swivel-up dispensing packages have been employed for dispensing personal care compositions in a topical way. Known swivel-up dispensing packages include a composition chamber, an applicator surface, a turn wheel that drives a feed screw and an elevator threadably engaged with the feed screw, which applies pressure to the composition as it is advanced towards the applicator surface. The composition may collapse onto the applicator surface following a normal dispensing and application event and this is an undesirable side effect of this type of dispensing package.

Accordingly, there exists a need for a dispensing package for applying a viscous composition directly on a target surface without contacting the composition in the dispensing package with his/her hands and to provide the composition in a stable unitary form on the applicator surface before applying to the target surface.

SUMMARY OF THE INVENTION

The present invention relates to a dispensing package for controlled delivery of a viscous composition on a target surface, the dispensing package comprising:
(a) a dispensing applicator comprising a container including an interior chamber for containing a viscous composition; and a dispensing head disposed about at least a portion of the container to define an outer end of the container; and
(b) a viscous composition disposed in the interior chamber;
wherein the dispensing head comprises:
(i) a front surface having a front surface centroid;
(ii) an opposing rear surface having a rear surface centroid;
(iii) a plurality of dispensing orifices extending therethrough, wherein the plurality of dispensing orifices are spaced apart and in fluid communication with the viscous composition contained within the interior chamber, wherein each of the plurality of dispensing orifices includes a front open end having a front centroid on the front surface, a rear open end having a back centroid on the rear surface, and a dispensing orifice axis extending through the front and back centroids; and
(iv) a center axis extending through the front surface centroid and the rear surface centroid and a plane extending along the center axis;
wherein a first dispensing orifice of the plurality of dispensing orifices has a first dispensing orifice axis inclined at a first orifice acute angle α1 (degrees) relative to the plane, so as to intersect the plane at a first point above the front surface.

DETAILED DESCRIPTION OF THE INVENTION

It has been found that the design of parts making up a dispensing package for controlled delivery of a viscous composition play an important role in enabling ease of applying the composition, preventing contact by hand. Specifically, when the composition is extruded through an orifice of the dispensing head above a predetermined height above the dispensing head, the extruded composition may separate from the remaining composition in the applicator and collapse onto the dispensing head. Collapsing of the extruded composition may result in an undesirable appearance on an exterior surface of the dispensing head. It has also been surprisingly found that providing a dispensing head designed with a plurality of dispensing orifices extending therethrough and having a first dispensing orifice axis inclined at an orifice acute angle relative to a plane extending along a center axis of the dispensing head so as to intersect the plane at a first point about a front surface of the dispensing head can help provide a controlled and stable extruded composition during dispensing.

The present invention relates to a dispensing package and a method for controlled delivery of a viscous composition (hereinafter "composition"). The dispensing package is suitable for various uses, including but not limited to, dispensing a cream or soft solid type composition, such as pharmaceutical products, personal care products and cosmetic products. The following description referring to the figures is intended to provide non-limiting examples of the present invention. It should be understood that other embodiments are contemplated, including embodiments with additional, fewer or alternative features and different combinations of the features shown and/or described.

In the following description, the dispensing package described is a consumer product, such as a personal care product, for dispensing a composition to a target surface to deliver a variety of benefits such as a therapeutic benefit or a cosmetic benefit. A personal care product may include but not limited to a cosmetic product, a therapeutic product or a deodorant product. However, it is contemplated that the dispensing package may be configured for use in a variety of applications to deliver compositions to the target surface and the dispensing package may include but is not limited to consumer products, such as, for example personal care products. In the following description, the composition described is a topical aromatic releasing composition containing petrolatum and one or more volatile aromatic compounds.

All weights, measurements and concentrations herein are measured at 25° C. on the composition in its entirety, unless otherwise specified.

Unless otherwise indicated, all percentages of compositions referred to herein are weight percentages and all ratios are weight ratios.

Unless otherwise indicated, all molecular weights are weight average molecular weights.

Unless otherwise indicated, the content of all literature sources referred to within this text are incorporated herein in full by reference.

Except where specific examples of actual measured values are presented, numerical values referred to herein should be considered to be qualified by the word "about".

Active and other ingredients useful herein may be categorized or described herein by their cosmetic and/or therapeutic benefit or their postulated mode of action. However, it is to be understood that the active and other ingredients useful herein can in some instances provide more than one cosmetic and/or therapeutic benefit or operate via more than one mode of action. Therefor classifications herein are made for the sake of convenience and are not intended to limit an ingredient to the particularly stated application or applications listed.

Prior to describing the present invention in detail, the following terms are defined for clarity. Terms not defined should be given their ordinary meaning as understood by a skilled person in the relevant art.

The term "dispensing orifice" as used herein refers to an opening in a dispensing head through which a composition is dispensed.

The term "start dose" as used herein refers to an amount of a composition dispensed from a dispensing package according to the present invention at first use of the dispensing package.

The term "dose" as used herein refers to an amount of a composition dispensed from a dispensing package according to the present invention at one time.

The term "vertical orientation" as used herein, refers to a position of a dispensing package according to the present invention wherein the front surface of the dispensing head is facing the environment in an upward facing position.

Figure 1:
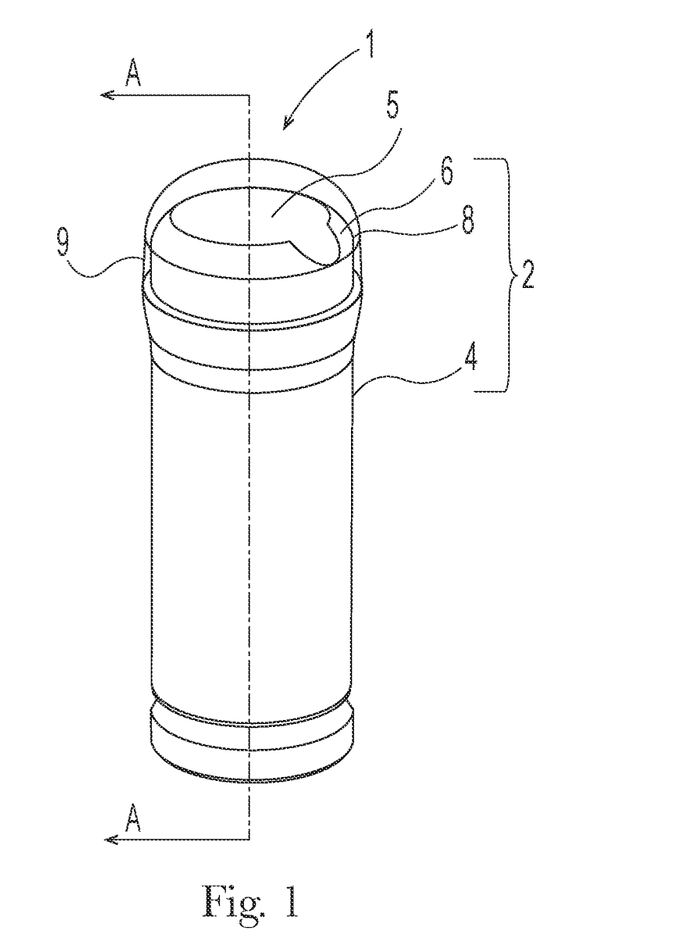
FIG. 1 is a perspective view of a dispensing package for controlled delivery of a viscous composition to a target surface according to the present invention.

FIG. 1 is a perspective view of a dispensing package 1 for controlled delivery of a viscous composition (hereinafter "composition"). In the following description the components of the dispensing package are molded from thermoplastic polymers suitable for injection molding and chemically compatible with the composition as described hereinafter. However, it is contemplated that the components may be made of any material depending on the manufacturing techniques and chemistry of the composition contained in the dispensing package 1.

Referring to FIG. 1, the dispensing package 1 comprises a dispensing applicator 2. The dispensing applicator 2 comprises a container 4 containing a composition and a dispensing head 6 disposed about at least a portion of the container 4 to define an outer end 8 of the dispensing applicator 2. A cap 9 can be attached to the dispensing head 6 to prevent dust and other contaminates from settling thereon. The cap 9 may be made of a transparent plastic material as shown in FIG. 1 or may be made of an opaque or translucent plastic material. However, the cap 9 may also be made of other materials capable of being shaped to cover the dispensing head 6, the materials including but not limited to metal, wood, silicone materials, and combinations thereof.

Further, a releasable adhesive seal 5 may be placed on the dispensing head 6. The releasable adhesive seal 5 functions as a protective barrier to prevent the composition from being exposed to air prior to use of the dispensing package 1. Specifically, the releasable adhesive seal 5 may be sized and shaped for covering dispensing orifices 30 described hereinafter with reference to FIGS. 2A, 2B, 3 and 4.

Figure 2A:
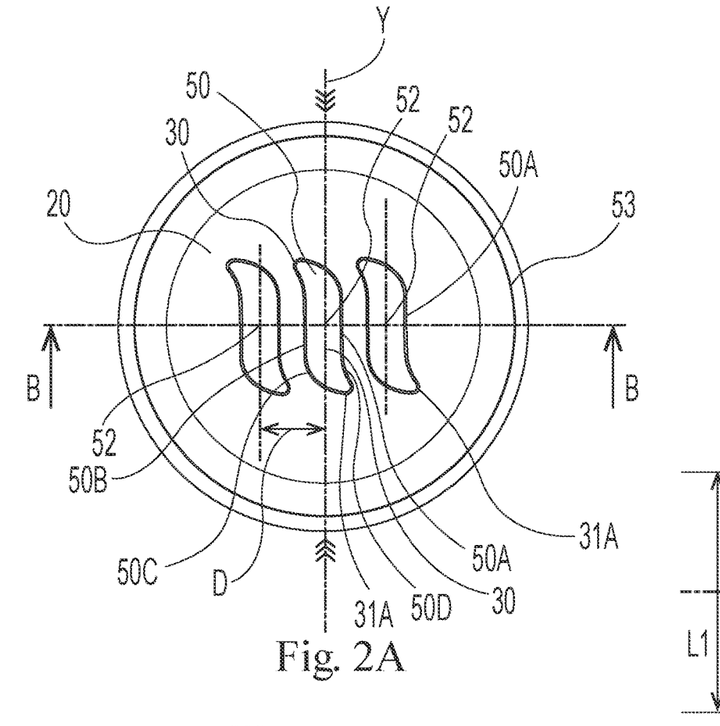
FIG. 2A is a top view of a dispensing head for a dispensing package of FIG. 1.

FIG. 2A is a top view of the dispensing head 6 of FIG. 1. The dispensing head 6 has a front surface 20 and a plurality of dispensing orifices 30 extending therethrough. The dispensing head 6 may comprise three dispensing orifices 30 spaced apart on the front surface 20. At least one of the dispensing orifices 30 includes a front open end 50 having a front centroid 52 on the front surface 20. The dispensing orifices 30 may be positioned on the front surface 20 and spaced apart with a front centroid-to-front centroid distance D from 4 mm to 12 mm, from 5 mm to 10 mm, from 6 mm to 8 mm, or different combinations of the upper and lower numerical values described above or combinations of any integer in the ranges listed above. A Y-axis may be drawn through the front centroid 52 on the top view of the dispensing head 6, and the dispensing orifices 30 may be positioned on the front surface 20 and spaced apart relative to a distance from the Y-axis. The dispensing head 6 may comprise a diameter 53 of 20 to 80 mm, from 30 to 60 mm, from 35 to 50 mm or different combinations of the upper and lower numerical values described above or combinations of any integer in the ranges listed above.

As shown in FIG. 2A, each or at least one of the dispensing orifices 30 may comprise a wave shape. However, it is contemplated that the dispensing orifices 30 may be of any shape which provides for uniform application and distribution of the composition. Specifically, the front open end 50 of the dispensing orifice 30 may comprise two edges 50A, 50B spaced apart to define a gap comprising a width (W1 shown in FIG. 2B). The edges 50A and 50B may be substantially parallel to each other and each comprises a length. Each opposing end of the edges 50A, 50B are joined by a convex curve 50C and a concave curve 50D to form a tip 31A, 31B of the dispensing orifice 30.

Figure 2B:
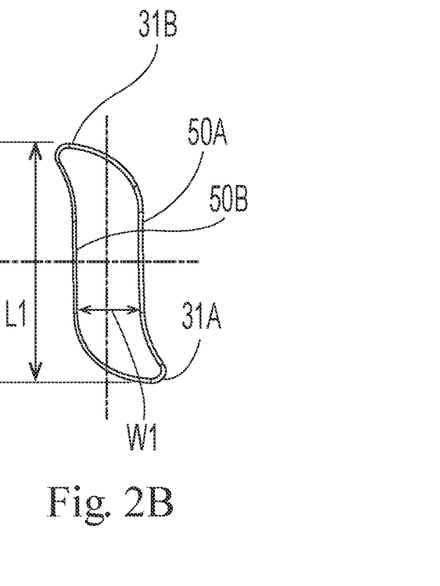
FIG. 2B is a detailed view of a dispensing orifice of the dispensing head of FIG. 2A.

FIG. 2B is a detailed view of the dispensing orifice 30 of FIG. 2A. The dispensing orifice 30 may comprise a dispensing orifice aspect ratio defined by a length (L1) defined between tip 31A and 31B to the width (W1) of the gap between the edges 50A, 50B. The dispensing orifice aspect ratio may be from 5:1 to 2:1, preferably 4:1 to 3:1, more preferably 4:1 or different combinations of the upper and lower limits described above or combinations of any integer in the ranges listed above. At least one of the dispensing orifices 30 may comprise a width W1 of from 1 to 8 mm, preferably 2 to 6 mm, more preferably from 3 to 5 mm, and a length L1 of from 9 to 15 mm, preferably 10 to 13 mm, more preferably 11 to 12 mm or different combinations of the upper and lower limits described above or combinations of any integer in the ranges listed above.

Figure 3:
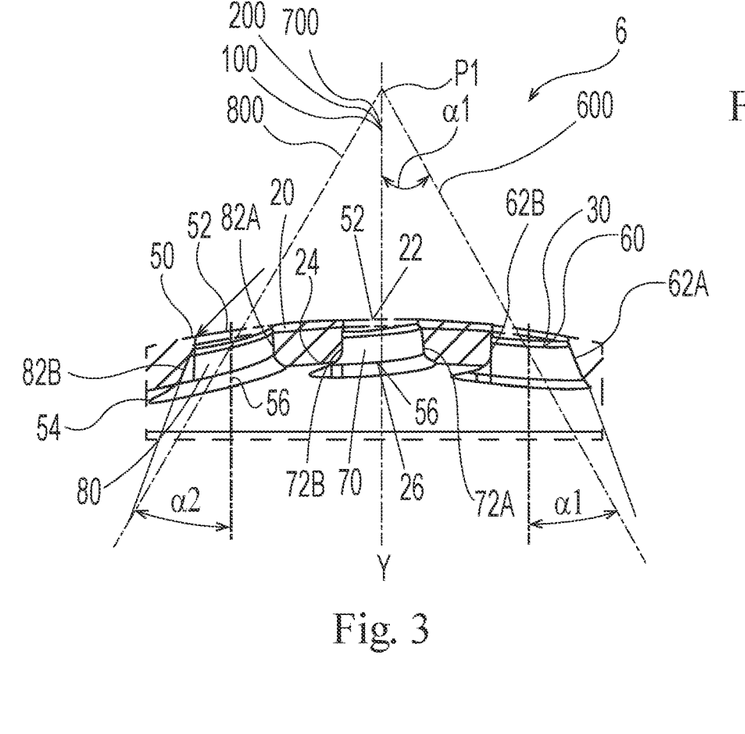
FIG. 3 is a side section detailed view of the dispensing orifices of the dispensing head of FIG. 2A.

FIG. 3 is a section view of the dispensing head 6 of FIG. 2A at the section line B-B. The front surface 20 of the dispensing head 6 has a front surface centroid 22 and an opposing rear surface 24 having a rear surface centroid 26. A center axis 100 is extending through the front surface centroid 22 and the rear surface centroid 24 and a plane 200 extending along the center axis 100. The dispensing orifice 30 further comprises a rear open end 54 having a back centroid 56 on the rear surface 24. The dispensing head 6 comprises a first dispensing orifice 60, a second dispensing orifice 70, and a third dispensing orifice 80. The first dispensing orifice 60 comprises a first dispensing orifice axis 600 inclined at a first orifice acute angle α1 (degrees) relative to the plane 200, so as to intersect the plane 200 at a first point P1 above the front surface 20. A technical effect of the first dispensing orifice axis 600 is that it enables dispensing of the composition upon rotation of a gripping portion operatively coupled to the dispensing applicator 2 through the first dispensing orifice 60 in the form of a unitary composition structure of the composition. An advantage of having a unitary structure is that a dosing of the composition may be metered and thus controlled dispensing of the composition to suit different consumer needs and usage patterns.

Referring to FIG. 3, the first dispensing orifice 60 includes a first dispensing orifice wall having a first orifice side 62A distal from and inclined at an acute angle relative to the center axis 100, and a second orifice side 62B opposite the first orifice side 62A. The second orifice side 62B is less inclined relative to the first orifice side 62A and a technical effect of having the sides 62A, 62B inclined at different angles relative to the center axis 100 is to guide dispensing of the composition to converge at the first point P1 as shown in the Example. Further, having the inclined orifice sides also improve moldability of the dispensing head 6, i.e. ease of release of the dispensing head 6 from the molding tool.

The second dispensing orifice 70 may comprise a second dispensing orifice axis 700 substantially parallel to the center axis 100. The second dispensing orifice axis 700 may be adjacent to the center axis 100, or along the center axis 100. The second dispensing orifice 70 may comprise a second dispensing orifice wall having orifice sides 72A, 72B designed in an symmetric way to the first dispensing orifice wall relative to the center axis 100 so that the same technical effect is achieved to obtain the composition delivery and/or moldability improvement advantages.

The third dispensing orifice 80 may comprise a third dispensing orifice axis 800 substantially inclined at a second orifice acute angle α2 (degrees) relative to the plane 200, so as to intersect the plane 200 at a first point (P1) above the front surface 20. The third dispensing orifice 80 may comprise a third dispensing orifice wall having orifice sides 82A, 82B designed in an symmetric way to the first dispensing orifice wall relative to the center axis 100 so that the same technical effect is achieved to obtain the composition delivery and/or moldability improvement advantages. It will be appreciated that the unitary composition structure may be generated with any two of the first dispensing orifice 60, the second dispensing orifice 70 and the third dispensing orifice 80.

The first orifice acute angle α1 may be from 1 degree to 70 degrees, from 2 to 50 degrees, from 3 to 40 degrees, from 5 to 30 degrees, from 5 to 20 degrees, or different combinations of the upper and lower numerical values described above or combinations of any integer in the ranges listed above relative to the plane 200. The second orifice acute angle α2 may be equal to or different from the first orifice acute angle α1.

Specifically, the first and second orifice acute angles α1, α2 may be configured such that the first dispensing orifice 60 is opposed to the third dispensing orifice 80 with the second dispensing orifice 70 intermediate the first and third dispensing orifices 60, 80 to converge towards the center axis 100 to create the unitary composition structure 14A.

The front open ends 50 of the first, second and third dispensing orifices 60, 70, 80 may comprise a total orifice cross-sectional area SA1 at the front surface 20, and the front surface 20 has a remaining front surface area SA2. SA1 may be less than or equal to SA2, SA1 may be from 5% to 49%, from 10% to 40%, from 15% to 30%, of SA2 or different combinations of the upper and lower percentages described above or combinations of any integer in the ranges listed above. SA1 may be from about 80 mm2 to about 150 mm2, from about 85 mm2 to about 110 mm2 or different combinations of the upper and lower areas described above or combinations of any integer in the ranges listed above.

Further, a front open end cross-sectional area SA3 of the front open end 50 of the first dispensing orifice 60 may be less than or equal to a rear open end cross-sectional area SA4 of the rear open end 54 of the first dispensing orifice 60. The front end cross-section area SA3 of the first dispensing orifice (60) may be less than the rear open end cross-sectional area SA4

The front open end cross-section area SA3 may be from 10 mm2 to 100 mm2, or adapted to provide a desired dose per rotation of a gripping portion. Still further, a front open end cross-sectional area SA5 of the second dispensing orifice 70 may be substantially equal to a front open end cross-sectional area SA3 of the front open end 50 of the first dispensing orifice 60.

The cross-sectional areas described hereinbefore are not illustrated in the figures. However, it will be appreciated that the front and back centroids 52, 56 and dimensions of above described features of the dispensing head 6 may be determined using conventional techniques including CAD (Computer Aided Design) software tools and standard measurement techniques and is described hereinafter under Test Methods, Feature Measurement Method and Example.

The dispensing head 6 may be designed to be integral with the container 4 or it could be designed as a separate unitary component from the container 4.

Figure 4:
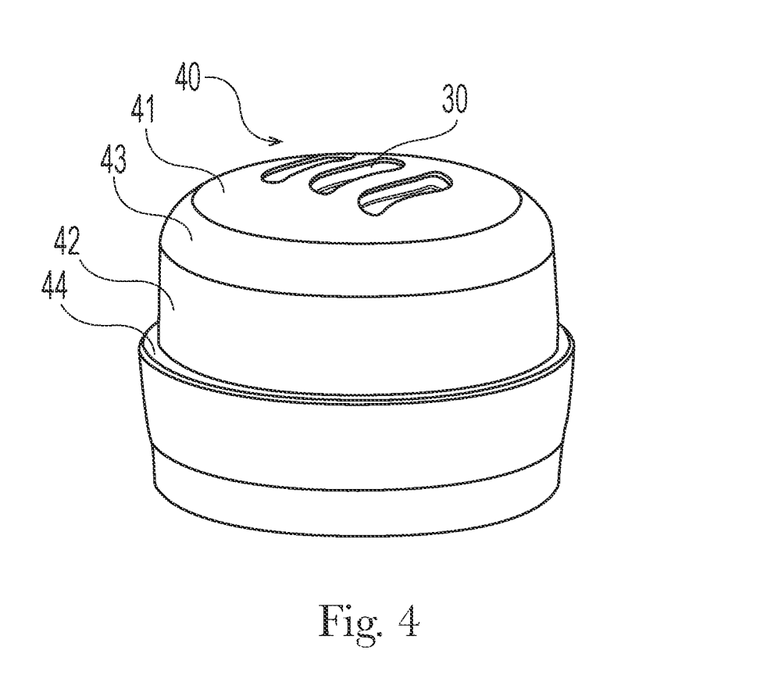
FIG. 4 is a perspective view of a unitary dispensing head according to the present invention.

FIG. 4 is a perspective view of a unitary dispensing head 40 according to the present invention. Specifically, the dispensing head 40 has substantially the same features as the dispensing head 6 of FIG. 2A and differs in the design of the dispensing orifices and shape of the dispensing head. The dispenser head 40 may be configured to be fixedly attached to the container 4 if the dispensing package 1 is a single use disposable product. The dispensing head 40 may also be releasably attached to the container 4. Having the dispensing head 40 manufactured as a separate component enables ease of flexibility in providing different product executions, such as for example if the container 4 containing the composition is sold as a refill for the dispensing package 1.

Specifically, the dispensing head 40 comprises a front surface 41, a plurality of dispensing orifices 30 extending therethrough, and a side wall 42 extending from the front surface 41 for circumscribing at least a part of the container 4 of FIG. 1. The front surface 41 of the dispensing head 40 may be generally curved or flat or any shape configured for adapting to a profile of the target surface on which the composition is applied.

Specifically, at least a front portion of the front surface 41 may be curved to define a curved front surface portion 43 having a curvature radius R from 10 mm to 100 mm, from 20 mm to 90 mm, from 30 mm to 80 mm, from 40 mm to 70 mm, or different combinations of the upper and lower numerical values described above or combinations of any integer in the ranges listed above, relative to a center point below the front surface 41. A front portion 43 having the specified curvature radius R provides a curved profile that enables a smoother touch by minimizing contact of edges of the dispensing orifices 30 against the skin of the consumer. Further, a dispensing head with a curved profile having the above curvature radius (R) also conforms well to any shape of a target surface of the human body to which the composition is applied and improves a feel experience upon contacting the dispensing head 6 to the target surface.

The side wall 42 may comprise a ledge 44 for receiving a cap such as the cap 9 of FIG. 1. The cap may be engaged to the dispensing head 40 through a threaded portion (not shown) arranged to engage with dispensing head screw threads (not shown) circumferentially disposed about the side wall 42. The cap may also be engaged by a full or partial snap bead circumferentially disposed about the side wall 42, a friction fit, or other conventional means.

The dispensing head 40 may comprise from four to eight dispensing orifices, wherein the dispensing orifices may be spaced apart, equally spaced apart, or radially spaced described hereinafter with respect to FIGS. 5, 6 and 7.

Alternative Designs of Dispensing Orifices

Figure 5:
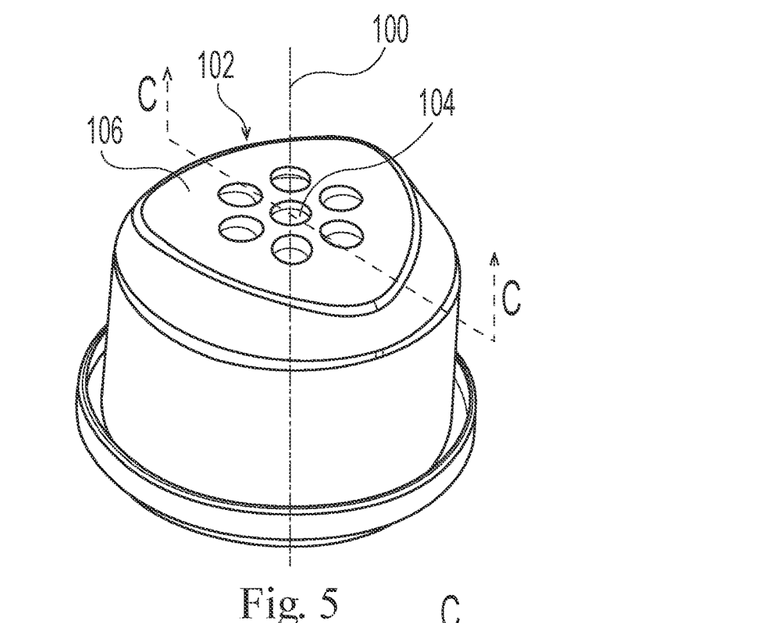
FIG. 5 is a perspective view of a dispensing head with a different design of dispensing orifices according to the present invention.

FIG. 5 is a perspective view of a dispensing head 102 with a plurality of an alternative design of dispensing orifices 104 for a dispensing package according to the present invention. The dispensing head 102 of FIG. 5 comprises substantially the same features as the dispensing head 6 of FIG. 1 and differs only in the shape of the dispensing head, the number and shape of the dispensing orifices and the angle of the dispensing orifice axis. Specifically, the dispensing head 102 comprises a plurality of dispensing orifices 104 radially spaced apart on a front surface 106 of the dispensing head 102. The dispensing orifices 104 each have a substantially circular shape.

Figure 6:
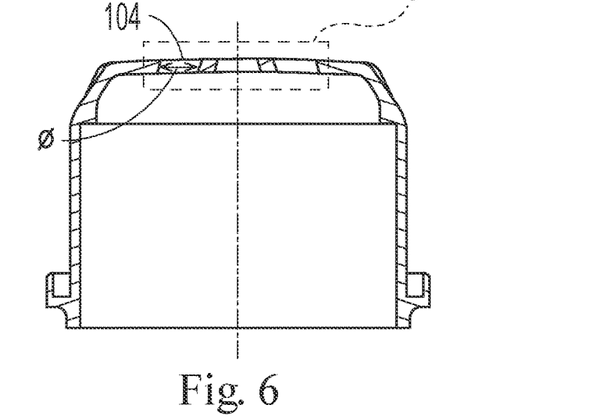
FIG. 6 is a side section view of the dispensing head of FIG. 5.

FIG. 6 is a side section view of the dispensing head 102 at section line C-C. At least one of the dispensing orifices 104 may comprise a diameter Ø from 1 to 10 mm, from 2 to 8 mm, from 3 to 6 mm.

Figure 7:
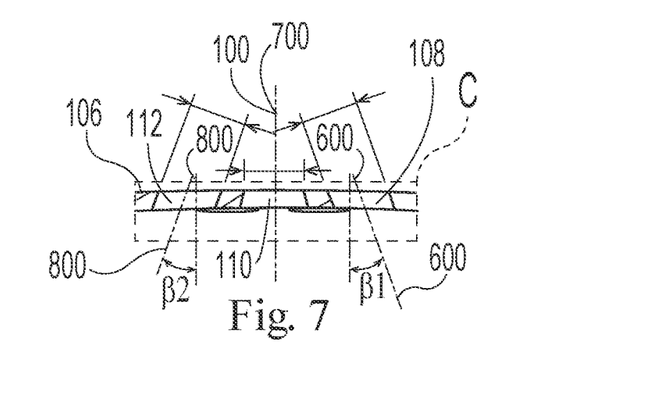
FIG. 7 is a detailed view of the side section view of the dispensing head of FIG. 6.

FIG. 7 is a detailed view of Detail C in the side section view of the dispensing head 102 of FIG. 6. Referring to FIG. 7, the dispensing head 102 comprises a first dispensing orifice 108, a second dispensing orifice 110, and a third dispensing orifice 112. The first dispensing orifice 108 comprises a first dispensing orifice axis 600 inclined at a first orifice acute angle β1 (degrees) relative to a plane comprising the center axis 100, so as to intersect the plane at a first point (not shown) above a front surface 106. A technical effect of the first dispensing orifice axis 600 is that it enables dispensing of the composition, upon rotation of a gripping portion of the dispensing package, through the first dispensing orifice 108 in the form of a unitary composition structure of the composition. An advantage of having a unitary structure is that a dosing of the composition may be metered and thus controlled dispensing of the composition to suit different consumer needs and usage patterns. The first dispensing orifice 108 may comprise a first dispensing orifice wall having orifice sides designed in a symmetric way to the first dispensing orifice wall relative to the center axis 100 so that the same technical effect is achieved to obtain the moldability improvement advantages.

The second dispensing orifice 110 may comprise a second dispensing orifice axis 700 substantially parallel to the center axis 100. The second dispensing orifice axis 700 may be adjacent to the center axis 100, or along the center axis 100. The second dispensing orifice 110 may comprise a second dispensing orifice wall having orifice sides designed in a symmetric way to the first dispensing orifice wall relative to the center axis 100 so that the same technical effect is achieved to obtain the moldability improvement advantages.

The third dispensing orifice 112 may comprise a third dispensing orifice axis 800 substantially inclined at a second orifice acute angle α2 (degrees) relative to the plane, so as to intersect the plane at a first point above the front surface 20. The third dispensing orifice 112 may comprise a third dispensing orifice wall having orifice sides designed in a symmetric way to the first dispensing orifice wall relative to the center axis 100 so that the same technical effect is achieved to obtain the moldability improvement advantages. It will be appreciated that the unitary composition structure may be generated with any two of the first dispensing orifice 108, the second dispensing orifice 110 and the third dispensing orifice 112.

The first orifice acute angle β1 may be from 1 degree to 70 degrees, from 2 to 50 degrees, from 3 to 40 degrees, from 5 to 30 degrees, from 5 to 20 degrees, or different combinations of the upper and lower numerical values described above or combinations of any integer in the ranges listed above relative to the plane. The second orifice acute angle β2 may be equal to or different from the first orifice acute angle β1.

Specifically, the first and second orifice acute angles β1, β2 may be configured such that the first dispensing orifice 108 is opposed to the third dispensing orifice 112 with the second dispensing orifice 110 intermediate the first and third dispensing orifices 108, 112 to converge towards the center axis 100 to create the unitary composition structure.

It will be appreciated that the dimensions and shapes of the features of the dispensing orifices in the dispensing head described and shown hereinbefore are only examples of one or more configurations, and any variety of dimensions and shapes may define the dispensing orifice as long as the design of the dispensing orifice provides an inclined dispensing orifice which enables the composition to converge to a point above the front surface.

Figure 8:
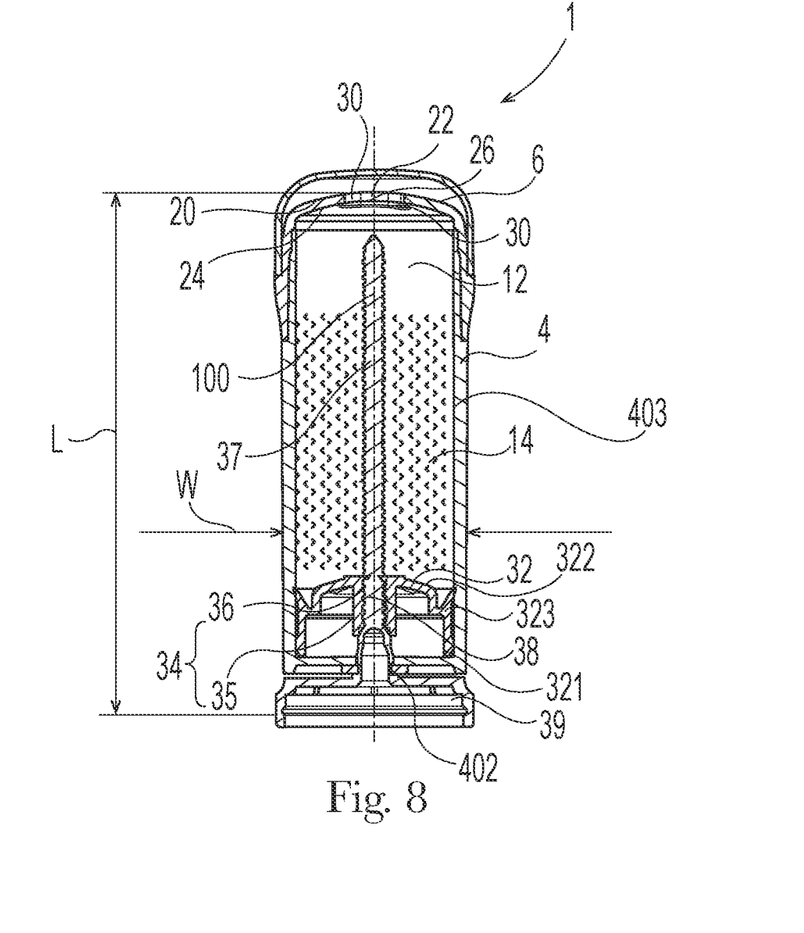
FIG. 8 is a side section view of components of the dispensing package of FIG. 1.

Details of how the dispensing orifices 30 and the dispensing head 6 is implemented in a dispensing package 1 according to the present invention is described with reference to FIG. 8. FIG. 8 is a side section view of the dispensing package 1 of FIG. 1 taken at section A-A.

The container 4 comprises an inner wall 403 defining an interior chamber 12 for containing a viscous composition 14. The dispensing orifices 30 is in fluid communication with the composition 14 contained within the interior chamber 12. The interior chamber 12 may comprise a volume from about 10 milliliters (ml) to about 200 ml, from 40 ml to about 150 ml, from about 60 ml to about 120 ml or different combinations of the upper and lower percentages described above or combinations of any integer in the ranges listed above. The interior chamber 12 may comprise a head space, a cross-sectional area of 15 cm2 and an axial length of 50 mm for containing 50 ml or 50 grams of the composition 14.

The dispensing package 1 may comprise an elevator 32, and an actuator system 37 for driving the elevator 32 towards the dispensing head 6. The actuator system 37 comprises a feed screw 38 and a gripping portion 39 operably coupled to the feed screw 38. It is contemplated that the feed screw 38 and the gripping portion 39 may be directly coupled or attached together through by known means such as a collar (not shown) which prevent separation or rotation of the feed screw 38 relative to the gripping portion 39. The actuator assembly 37 is operably connected to the elevator 32 wherein rotation of the gripping portion 39 advances the elevator 32 towards the dispensing head 6. The dispensing package 1 may further comprise a gasket for sealing a junction between the feed screw 38 and the elevator 32.

The container 4 has a centrally located hole 402 located at a base of the container 4 for receiving the feed screw 38. The interior chamber 12 comprises a volume, wherein the volume of the interior chamber 12 may be defined as a product of its cross-sectional area and an effective distance between the elevator 32 and the rear surface 24 of the dispensing head 6. The elevator 32 is axially movable within an interior chamber 12 of the container 4 in a direction parallel to the center axis 100. The elevator 32 may have a cross-sectional area corresponding to the cross-sectional area of the interior chamber 12.

The elevator 32 further comprises an elevator platform and a coupling sleeve 34 centrally disposed in the elevator platform for coupling to the feed screw 38. The elevator platform may comprise an elevator base 321 and an elevator top 322 spaced apart from the elevator base 321 to define a height of the elevator platform wherein the elevator top 322 has a surface upon which the composition 14 is disposed.

The coupling sleeve 34 has a threaded section 35 for engaging the feed screw 38 and a non-threaded section 36 for connecting to the gripping portion 39. FIG. 3 shows the elevator 32 in a ground position proximal to a container base 401 of the container 4. A bottom of the interior chamber 12 is defined by a position of the elevator top 322 relative to the feed screw 38 as the elevator 32 moves toward the dispensing head 6, and according a volume of the head space 13 changes. The elevator 32 may further comprise a peripheral wall 323 extending between the elevator top 322 and the elevator base 321 wherein the peripheral wall 323 is configured for engaging the inner wall 403 of the container 4. The peripheral wall 323 may have an upper sealable end and a lower sealable end which bears against the inner wall 403 so as to create a seal between the interior chamber 12 and the container base 401. As the elevator 32 is threadably connected to the feed screw 38 that is connected to the gripping portion 39, the elevator 32 is movable relative to the inner wall 403 of the container 4 upon rotation of the gripping portion 39 to displace the composition 14 along the center axis 100 and through the dispensing orifices 30 of the dispensing head 6.

The dispensing package 1 may be sized and shaped to allow the dispensing package 1 to be portable for travel. The dispensing package 1 may be sized and shaped to fit comfortably in the palm of the hand. The dispensing package 1 may have an aspect ratio (applicator width W:applicator length L) of at least 1:5, preferably from 1:5 to 1:1, more preferably from 1:4 to 1:1, even more preferably from 1:3 to 1:2, even yet more preferably 1:3.

The container 4, the feed screw 38 and the elevator 32 may be molded from polypropylene or other suitable material compatible with the composition 14. Specifically, the feed screw 38 and the elevator 32 may be molded from a polymer selected from the group consisting of: acrylonitrile butadiene styrene, blend of polyphenylene ether and polystryrene, high density polyethylene, nylon, styrene acrylonitrile, polyethylene terephthalate glycol, polybutylene terephthalate, and mixtures thereof.

Method

The present invention also relates to a method of delivering a dose of the composition 14 on a target surface, the method comprising the steps of providing a dispensing package 1 according to the present invention and moving the elevator 32 of the dispensing package 1 to advance the composition 14 upstream from the rear surface 24 to the front surface 20 to enable controlled delivery of a composition 14 on a target surface.

To explain the way the dispensing orifices 30 and the actuator system 37 work to provide a controlled delivery of a composition 14 according to the present invention, it is helpful to understand how the composition 14 and the elevator 32 are advanced in operation. The method of delivering a composition 14 according to the present invention is described with reference to FIGS. 9A, 9B and 9C which are schematic drawings illustrating the movement of the elevator 32 and the composition 14 thereon.

Figure 9A:
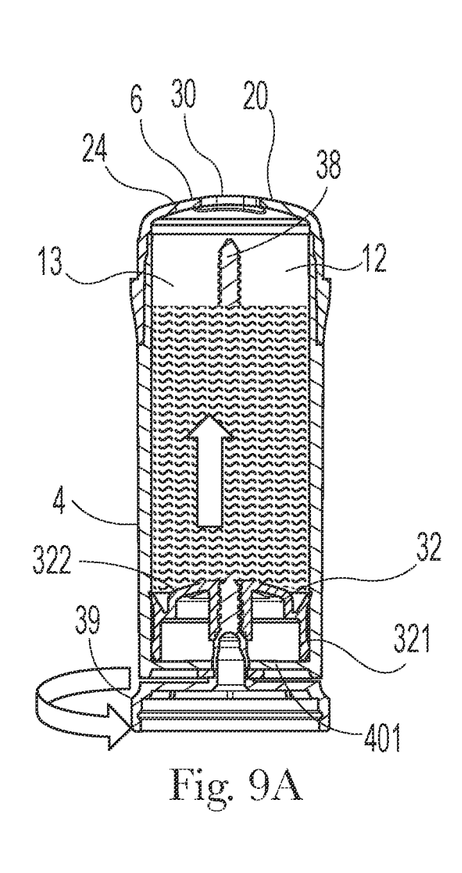
FIGS. 9A to 9C are schematic drawings which show the movement of a viscous composition through the dispensing orifices in a dispensing package according to the present invention.
Figure 9B:
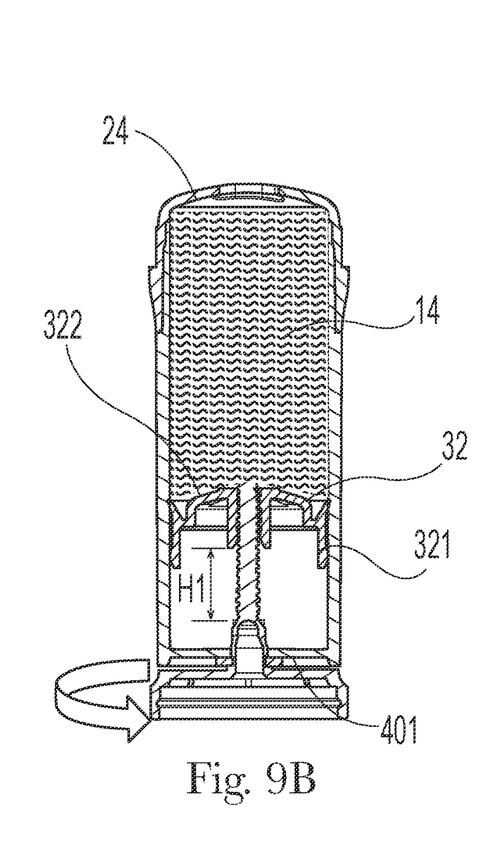
Figure 9C:
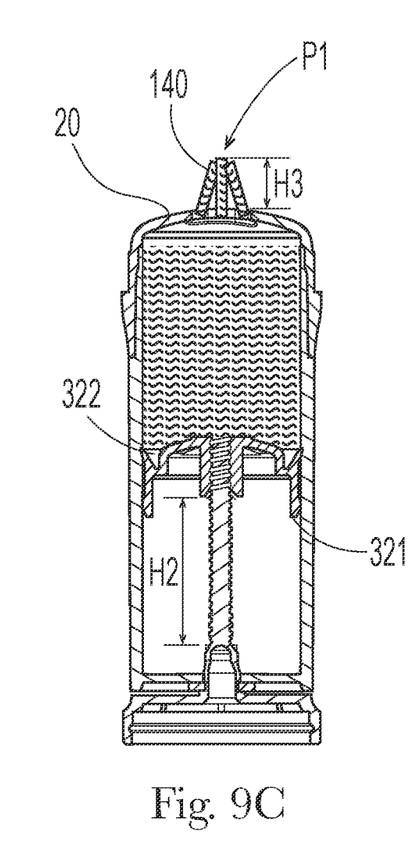

In FIGS. 9A, 9B and 9C, the dispensing package 1 is in a substantially vertical orientation. The interior chamber 12 of the container 4 is partially filled with the composition 14 with a headspace in the interior chamber. FIG. 9A illustrates a first step 9A of the method in which the elevator 32 is in a "ground" position wherein the elevator base 321 is proximal to a container base 401 of the container 4. FIG. 9B illustrates a second step 9B of the method in which the elevator 32 is moved axially within the interior chamber 12 in a direction Y1 parallel to the center axis 100 and FIG. 9C illustrates a third step 5C of the method in which the composition 14 is extruded through the dispensing orifices 30 into the atmosphere and above the front surface 20 of the dispensing head 6.

Referring to FIG. 9A, the elevator top 322 may be shaped to conform to a shape of the rear surface 24 of the dispensing head 6 so that most of the composition 14 will be dispensed when the elevator 32 is advanced to the dispensing head 6.

In operation, as the user rotates the gripping portion 39, there is a first axial displacement H1 of the feed screw 38 and the elevator 32 as shown in FIG. 9B. As a result of the axial displacement H1, the elevator 32 travels in an upward direction such that the elevator base 321 is distal to the container base 401. The composition 14 is also carried by the elevator 32 towards the rear surface 24 of the dispensing head 6. The gripping portion 39 may comprise a plurality of ridges (not shown) on the exterior of the gripping portion 39 wherein the ridges may be configured to provide a textured feel and increased friction during handling of the dispensing package 1 thereby improving a gripping action. For example, having an improved gripping action may facilitate users when rotating the gripping portion 39 to dispense the composition 14 on a target surface.

Referring to FIG. 9C, further rotation of the gripping portion 39 causes the elevator 32 to advance by a second axial displacement H2, wherein H2 is greater than H1 and H2 is an effective distance enough to extrude at least a portion of the composition 14 through the dispensing orifices 30 into the atmosphere thereby forming an extruded portion 140 of the composition 14. As the extruded portion 140 of the composition 14 is a self-supporting structure and does not collapse onto the front surface 20 of the dispensing head 6, this minimizes mess between each use and enables a controlled delivery of the composition 14 to a target surface. In the Examples described hereinafter, results indicating the height of the extruded portion 140 of the composition 14 at each rotation demonstrate structural stability of the composition when dispensed using the dispensing applicator according to the present invention.

Composition

Active and other ingredients useful herein may be categorized or described herein by their cosmetic and/or therapeutic benefit or their postulated mode of action. However, it is to be understood that the active and other ingredients useful herein can in some instances provide more than one cosmetic and/or therapeutic benefit or operate via more than one mode of action. Therefore, classifications herein are made for the sake of convenience and are not intended to limit an ingredient to the particularly stated application or applications listed.

The composition 14 may be a personal care composition adapted in any form suitable for consumer use for application to a target surface. The composition 14 may be formulated as a leave-on composition or a rinse-off composition. As used herein, "leave-on compositions" includes products that are intended to be applied to a bodily surface of a consumer such as the skin or hair and maintained on the surface for a prolonged time, preferably at least 5 minutes, more preferably at least 30 minutes, without being actively removed by washing, rinsing, wiping, rubbing or other forms of mechanical removal. As used herein, "rinse-off compositions" includes compositions that are intended to be applied to a bodily surface of a consumer, such as the skin or hair, and subsequently removed by washing, rinsing, wiping, rubbing or other forms of mechanical removal within less than 5 minutes of application.

The composition 14 may be formulated as a lotion, a cream, a gel, an ointment, or a paste. The composition 14 may comprise a viscosity from at least 1 centistoke (cSt), from about 1 to 30 cSt, from about 3 to about 20 cSt, from about 3 to about 15 cSt or different combinations of the upper and lower numerical values described above or combinations of any integer in the ranges listed above when measured at 100° C. Viscosity herein is measured on the composition using method ASTM D-445. The viscosity as described hereinbefore enables a more stable structure of the composition 14 when dispensed through the dispensing orifices 30 such as shown in the experimental data described hereinafter under EXAMPLES.

The composition 14 may comprise:
 a) from 0.01% to 15% of an essential oil;
 b) from 0.01% to 10% of a terpene material;
 c) a carrier; and
 d) optionally from 0.0001% to 0.01% of an auxiliary fragrance material different from the essential oil.

The carrier may be any material capable of carrying and delivering the fragrance materials herein in a stable and consumer-aesthetic form. Such carriers must also be suitable for application to the skin, hair, oral mucosa, preferably the skin (i.e. topical application), more preferably sensitive skin such as that of a baby. Suitable carriers include $C_2$ to $C_6$ monohydric alcohols, petrolatum, fluid silicone materials such as dimethicones, or mixtures thereof. The composition may comprise from about 1% to about 99.9799%, from about 40% to about 95%, more preferably still from about 50% to about 93% or different combinations of the upper and lower numerical values described above or combinations of any integer in the ranges listed above of a carrier by weight of the composition.

Specifically, the carrier may be petrolatum and the composition may comprise from about 40% to about 95%, from 70% to about 90%, or different combinations of the upper and lower numerical values described above or combinations of any integer in the ranges listed above of petrolatum by weight of the composition. The petrolatum may comprise a viscosity of 1 to 30 centistokes (cSt), from 2 to 20 cSt, from 3 to 15 cSt, from 5 to 10 cSt or different combinations of the upper and lower numerical values described above or combinations of any integer in the ranges listed above when measured at 100° C. based on ASTM D-445.

The composition 14 may comprise an essential oil selected from the group consisting of menthol, camphor, eucalyptol and mixtures thereof. The essential oil may be in an amount from about 0.1% to about 30%, from about 0.5% to about 20%, from about 1% to about 15%, from about 1.5% to 10% or different combinations of the upper and lower percentages described above or combinations of any integer in the ranges listed above, by weight of the composition. The essential oil may comprise eucalyptol. Eucalyptol is also known as 1,8-cineole, and is a terpene-like material isolated from and named for eucalyptus essential oil. Eucalyptol is widely found in essential oils and used in synthetic fragrances in varying amounts. It is thought to be an important component of eucalyptus oil and other essential oils, and responsible for a wide variety of activities and fragrances associated therewith. Eucalyptol generally has a chemical structure as set out below:

The composition 14 may comprise from about 0.01% to about 15% of eucalyptol. Preferably the composition 14 may comprise from about 0.1% to about 10%, from about 0.2% to about 8%, from about 0.5% to about 5% or different combinations of the upper and lower numerical values described above or combinations of any integer in the ranges listed above of eucalyptol by weight of the composition.

Eucalyptol is commercially available extracted from natural sources such as eucalyptus oil. Suitable examples of commercially available sources include eucalyptol available from Symrise (UK), Frey and Lau (UK) or FDL (UK).

The composition 14 may further comprise a terpene material. Said terpene material comprises α-pinene, β-pinene, α-phellandrene, para-cymene or mixtures thereof. Without wishing to be bound by theory, it is believed that the terpene material is useful herein, in combination with the allergenic fragrance material, for generating the characteristic fragrance notes, and providing effects such as relaxation, calming, muscle relaxation and analgesia associated with essential oils such as eucalyptus, rosemary and lavender.

The composition 14 may comprise from about 0.01% to about 10%, from about 0.1% to about 6%, from about 0.5% to about 5%, from 0.5% to 4% of a terpene material by weight of the composition. The terpene material may be selected from the group consisting of α-pinene, β-pinene, α-phellandrene, para-cymene and mixtures thereof. The above terpene materials correspond to the chemicals having the structure as set out in the table below.

| Name | Structure |
|---|---|
| α-pinene | α-Pinen |
| β-pinene | β-Pinen |
| α-phellandrene | |
| Para-cymene | |

The composition 14 may comprise from about 0.0001% to about 0.01% of an auxiliary fragrance material. The auxiliary fragrance material may be selected from the group consisting of: amyl cinnamal, benzyl alcohol, cinnamyl alcohol, citral, eugenol, hydroxy-citronellal, isoeugenol, amylcin-namyl alcohol, benzyl-salicylate, cinnamal, coumarin, geraniol, hydroxy-methylpentylcyclohexanecarboxaldehyde, anisyl alcohol, benzyl cinnamate, farnesol, 2(4-tert-butylbenzylpropionaldehyde), linalool, benzyl benzoate, citronellol, hexyl cinnam-aldehyde, limonene, methyl heptin carbonate, 3-methyl-4-(2,6,6-tri-methyl-2-cyclohexen-1-yl)-3-buten-2-one, and mixtures thereof. The auxiliary fragrance material may comprise limonene, linalool, benzyl alcohol, geraniol or mixtures thereof.

The terpene material and the auxiliary fragrance material may be formulated in the composition in ratios that enable the materials to act synergistically to provide fragrance and active benefits, whilst not generating a sensitivity-type response. Without being limited by theory, it is believed that both the auxiliary fragrance materials and terpene materials are essential to elicit the consumer response to essential oils, however, the combination herein allows the amount of auxiliary fragrance material present to be limited whilst still providing fragrance and active benefits. Preferably the ratio of terpene material to auxiliary fragrance material is from about 1:1 to about 1:10000, more preferably from about 1:10 to about 1:1000.

The following examples are intended to more fully illustrate the present invention and are not to be construed as limitations of the present invention since many variations thereof are possible without departing from the scope of the present invention. All parts, percentages and ratios used herein are expressed as percent weight unless otherwise specified.

Examples

Test equipment/materials and test composition are first described under Materials, then Test Methods are provided, and lastly results are discussed. Data is provided demonstrating the dispensing package of the present invention having improved delivery of a composition. Equipment and materials used in the Test Methods described hereinafter are listed in Table 1 below. The formulation of the test composition is provided in Table 2 below.

Materials

TABLE 1

| Equipment/Materials | |
|---|---|
| Component | Example |
| Weighing Scale | Conventional Weighing Scale |
| Composition | Test Composition Weight-37 grams |
| Dispensing Package | As shown in FIG. 8 |
| Dispensing Head | As shown in FIGS. 2, 3 |
| Dispensing Orifice | As shown in FIGS. 2, 3 |

The test composition evaluated is an aromatic releasing ointment commercially available as Vicks® VapoRub™ Cough Suppressant Topical Analgesic Ointment from Procter & Gamble (Record ID 6404813 on Mintel website at the following link—https://www.gnpd.com/sinatra/record-page/6404813/?utm_source=fed_search). The formulation example of the test composition is provided in Table 2 below. It will be appreciated other compositions suitable for use in the dispensing package may be formulated using techniques known to those skilled in the art and the following example is illustrative only, and not intended to limit the scope of the present invention.

TABLE 2

| Test Composition | | |
|---|---|---|
| Ingredient | Chemical Name | % by weight of the composition |
| Carrier | Petrolatum | 70% to 90% |
| Essential Oil | Camphor | 4.8% |
| Essential Oil | Eucalyptus oil | 1.2% |
| Essential Oil | Menthol | 2.6% |
| | Other ingredients not disclosed by manufacturer | Up to 100% |
| | Total | 100% |
| | pH (1% solution) | 7 to 9 |
| | Viscosity (Centistokes @ 100 degrees Celsius as determined by ASTM D-445) | 4 to 12 |

Dispensing Efficacy Test Method

This test method is used to evaluate a dispensing efficacy of a dispensing applicator according to the present invention. The test method is performed under the following test conditions: at an average temperature of 20° C. to 24° C. and an average % relative humidity of 30% to 60%. The steps for performing the test include:

Step 1: The weight of the dispensing applicator and the composition individually is measured using a weighing scale.

Step 2: The dispensing applicator is filled with 37 grams of the Test Composition.

Step 3: The weight of the dispensing applicator containing the composition is measured using a weighing scale.

Step 4: The gripping portion 39 of the dispensing applicator 2 is rotated five (5) times to advance the composition to the rear surface of the dispensing head (due to the head space of the interior chamber) to define a "ground" position of the elevator before a "start dose". An exemplary "ground" position is illustrated in FIG. 9B.

Step 5: To dispense a single dose of the composition, the gripping portion 39 of the dispensing applicator 2 is rotated to axially advance the feed screw such that there is an extruded portion of the composition above the front surface defining an unitary composition structure. An exemplary extruded portion 140 is shown in FIG. 9C.

Step 6: The height of the unitary composition structure is measured by measuring a distance between the tip of the extruded portion 140 to the front surface 20.

Step 7: The unitary composition structure is wiped off to prepare for the next application.

Step 8: The weight of the applicator and composition is measured at each rotation after the start dose.

Step 9: Steps 5 to 8 are repeated until a minimum level of composition is dispensed.

Step 10: The weight of remaining composition in the applicator is measured.

Feature Measurement Method

Dimensional features of the dispensing package and components may be measured using commercially available measurement systems. An exemplary measurement method for measurement of dimensional features of a physical component may comprise the following steps:

Step 1: Scan the physical component with commercially available 3D scanning software;

Step 2: Generate cad data based on the scanned physical component;

Step 3: Convert the cad data into a CAD software readable format, e.g. Catia software readable format.

Step 4: Measure dimensional features of the cad data in the CAD software.

Example

Table 3 shows a relation between each rotation, weight of the composition and a height of the extruded portion of the composition above the front surface at one time.

TABLE 3

| Rotation | Height of the unitary composition structure relative to the front surface as shown in FIG. 9C (mm) | Weight of Composition in the container (grams) | Weight of the unitary composition structure as shown in FIG. 9C (grams) | Average weight of unitary composition structure per rotation (grams) |
|---|---|---|---|---|
| 0 |  | 69.701 |  |  |
| 1 | 2.8 | 68.246 | 1.455 |  |
| 2 | 2.8 | 66.545 | 1.701 | 1.8 |
| 3 | 2.8 | 64.79 | 1.755 |  |
| 4 | 2.8 | 62.998 | 1.792 |  |
| 5 | 2.8 | 61.278 | 1.720 |  |
| 6 | 2.8 | 59.470 | 1.808 |  |
| 7 | 2.8 | 57.701 | 1.769 |  |
| 8 | 2.8 | 55.932 | 1.769 |  |
| 9 | 2.8 | 54.055 | 1.877 |  |
| 10 | 2.8 | 52.265 | 1.790 |  |
| 11 | 2.8 | 50.478 | 1.787 |  |
| 12 | 2.8 | 48.639 | 1.839 |  |
| 13 | 2.8 | 46.820 | 1.819 |  |
| 14 | 2.8 | 45.005 | 1.815 |  |
| 15 | 2.8 | 43.165 | 1.840 |  |
| 16 | 2.8 | 41.339 | 1.826 |  |
| 17 | 2.8 | 39.591 | 1.748 |  |
| 18 | 2.8 | 37.782 | 1.809 |  |
| 19 | 2.8 | 35.951 | 1.831 |  |
| 20 | 2.8 | 35.620 | 0.331 |  |
| Remaining weight of Composition in the applicator (grams) |  | 2.900 |  |  |

The above results of the height of the composition show that dispensing the composition 14 using a dispensing applicator 2 with dispensing orifices 30 according to the present invention enables a stable unitary composition structure 14A to be delivered to a target surface per rotation.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dispensing package (1) for controlled delivery of a viscous composition on a target surface, the dispensing package (1) comprising:
   (a) a dispensing applicator (2) including a container (4) including an interior chamber (12) for containing a viscous composition (14), and a dispensing head (6) disposed about at least a portion of the container (4) to define an outer end (8) of the container (4); and
   (b) a viscous composition (14) disposed within the interior chamber (12);
   wherein the dispensing head (6) comprises:
      (i) a front surface (20) having a front surface centroid (22), wherein the front surface is flat or curved in a convex manner;
      (ii) an opposing rear surface (24) having a rear surface centroid (26);
      (iii) a plurality of dispensing orifices (30) extending therethrough, wherein the plurality of dispensing orifices (30) are spaced apart and in fluid communication with the viscous composition (14) contained within the interior chamber (12), wherein each of the plurality of dispensing orifices (30) includes a front open end (50) having a front centroid (52) on the front surface (20), a rear open end (54) having a back centroid (56) on the rear surface (24), and a dispensing orifice axis (400) extending through the front and back centroids (52, 56); and
      (iv) a center axis (100) extending through the front surface centroid (22) and the rear surface centroid (24) and a plane (200) extending along the center axis (100);
   wherein a first dispensing orifice (60) of the plurality of dispensing orifices (30) has a first dispensing orifice axis (600) inclined at a first orifice acute angle α1 (degrees) relative to the plane (200), so as to intersect the plane (200) at a first point (P1) above the front surface (20),
   wherein the first orifice acute angle α1 is from 1 degree to 70 degrees.

2. The dispensing package (1) according to claim 1, wherein the composition (14) comprises a viscosity from at least 1 centistoke (cSt) at 100 degrees Celsius.

3. The dispensing package (1) according to claim 1, wherein the composition (14) comprises from about 40% to about 95%, by weight of the composition, of petrolatum, wherein the petrolatum comprises a viscosity of 1 to 30 centistokes (cSt) at 100 degrees Celsius.

4. The dispensing package (1) according to claim 1, wherein the composition (14) comprises:

(a) from about 0.25% to about 15%, by weight of the composition, of an essential oil comprising eucalyptol, camphor, menthol, or combinations thereof;
(b) optionally from about 0.01% to about 10%, by weight of the composition, of a terpene material comprising α-pinene, β-pinene, α-phellandrene, para-cymene, or combinations thereof; and
(c) optionally from about 0.0001% to about 0.01%, by weight of the composition, of an auxiliary fragrance material comprising amyl cinnamal, benzyl alcohol, cinnamyl alcohol, citral, eugenol, hydroxy-citronellal, isoeugenol, amylcin-namyl alcohol, benzyl-salicylate, cinnamal, coumarin, geraniol, hydroxy-methylpentyl-cyclohexanecarbox-aldehyde, anisyl alcohol, benzyl cinnamate, farnesol, 2(4-tert-butylbenzylpropion-aldehyde), linalool, benzyl benzoate, citronellol, hexyl cinnam-aldehyde, limonene, methyl heptin carbonate, 3-methyl-4-(2,6,6-tri-methyl-2-cyclohexen-1-yl)-3-buten-2-one, or combinations thereof.

5. The dispensing package (1) according to claim 1, wherein the composition (14) is a topical aromatic releasing ointment, wherein the composition (14) comprises turpentine.

6. The dispensing package (1) according to claim 1, wherein the front open ends (50) of the plurality of dispensing orifices (30) has a total orifice cross-sectional area SA1 at the front surface (20), and the front surface (20) has a remaining front surface area SA2, wherein SA1≤SA2.

7. The dispensing package (1) according to claim 1, wherein at least a portion of the front surface (41) is curved to define a curved front surface portion (43) having a curvature radius (R) of 1 mm to 15 mm relative to a center point below the front surface (41).

8. The dispensing package (1) according to claim 1, wherein a front end cross-sectional area SA3 of the front open end (50) of the first dispensing orifice (60) is less than or equal to a rear open end cross-sectional area SA4 of the rear open end (54) of the first dispensing orifice (60), wherein SA3 is from 10 mm² to 100 mm².

9. The dispensing package (1) according to claim 1, wherein at least a portion of the plurality of dispensing orifices (30) are spaced apart about the center axis (100).

10. The dispensing package (1) according to claim 1, wherein a second dispensing orifice (70) of the plurality of dispensing orifices comprises a second dispensing orifice axis (700) parallel to the center axis (100).

11. The dispensing package (1) according to claim 1, wherein the plurality of dispensing orifices (30) comprises a second dispensing orifice (70), wherein a front end cross-sectional area SA5 of the second dispensing orifice (70) is equal to a front end cross-sectional area SA3 of the first dispensing orifice (60).

12. The dispensing package (1) according to claim 1, wherein a third dispensing orifice (80) of the plurality of dispensing orifices (30) comprises a third dispensing orifice axis (800) inclined at a second orifice acute angle α2 (degrees) relative to the plane (200), so as to intersect the plane (200) at the first point (P1) above the front surface (20).

13. The dispensing package (1) according to claim 1, wherein the dispensing head (6) is operably attached to the container (4).

14. The dispensing package (1) according to claim 1, further comprising:
an elevator (32) axially movable within the interior chamber (12) in a direction parallel to the center axis (100), wherein the elevator (32) comprises an elevator platform and a coupling sleeve (34) having a threaded section (36);

an actuator assembly (37) comprising a feed screw (38) movably connected to the threaded section (36) of the coupling sleeve (34);

a gripping portion (39) operably connected to the elevator (32);

wherein rotation of the gripping portion (39) advances the elevator platform toward the dispensing head (6);

optionally, the interior chamber (12) comprises a volume from about 10 ml to about 200 ml.

15. The dispensing package (1) according to claim 14, wherein the feed screw (38) is configured to advance the elevator platform to obtain an unitary composition structure (14A) having an average weight of at least 1.8 grams per rotation of the gripping portion (39).

16. The dispensing package (1) according to claim 14, wherein the feed screw (38) and the elevator platform are molded from a polymer comprising acrylonitrile butadiene styrene, blend of polyphenylene ether and polystryrene, high density polyethylene, nylon, styrene acrylonitrile, polyethylene terephthalate glycol, polybutylene terephthalate, or mixtures thereof.

17. A method of delivering a dose of a viscous composition (14) on a target surface, the method comprising the steps of:
(i) providing a dispensing package (1) according to claim 1; and
(ii) applying a force to the dispensing package to move the composition (14) upstream from the rear surface (22) to the front surface (21) to enable controlled delivery of the composition (14) on the target surface.

18. A dispensing applicator (2) for a dispensing package (1) for delivering a dose of a viscous composition (14) on a target surface, the dispensing applicator (2) comprising:
(a) a container (4) including an interior chamber (12) for containing a viscous composition (14), and
(b) a dispensing head (6) disposed about at least a portion of the container (4) to define an outer end (8) of the container (4); wherein the dispensing head (6) comprises:
(i) a front surface (20) having a front surface centroid (22), wherein the front surface is flat or curved in a convex manner;
(ii) an opposing rear surface (24) having a rear surface centroid (26);
(iii) a plurality of dispensing orifices (30) extending therethrough, wherein the plurality of dispensing orifices (30) are spaced apart and in fluid communication with the viscous composition (14) contained within the interior chamber (12);

wherein each of the plurality of dispensing orifices (30) includes a front open end (50) having a front centroid (52) on the front surface (20), a rear open end (54) having a back centroid (56) on the rear surface (24), and a dispensing orifice axis (400) extending through the front and back centroids (52, 56); and a center axis (100) extending through the front surface centroid (22) and the rear surface centroid (26) and a plane (200) extending along the center axis (100);

wherein a first dispensing orifice (60) of the plurality of dispensing orifices (30) has a first dispensing orifice axis (600) inclined at a first orifice acute angle α1 (degrees) relative to the plane (200), so as to intersect the plane (200) at a first point (P1) above the front surface (20), wherein the first orifice acute angle α1 is from 1 degree to 70 degrees;

(iv) wherein the composition (14) comprises from 40% to 95%, by weight of the composition, of petrolatum, wherein the petrolatum comprises a viscosity of 1 to 30 centistokes (cSt) at 100 degrees Celsius.

19. The dispensing applicator according to claim 18, wherein the composition (14) comprises:
(a) from 0.25% to 15%, by weight of the composition, of an essential oil comprising eucalyptol, camphor, menthol, or combinations thereof;
(b) optionally, from 0.01% to 10%, by weight of the composition, of a terpene material comprising α-pinene, β-pinene, α-phellandrene, para-cymene, or combinations thereof; and
(c) optionally, from 0.0001% to 0.01%, by weight of the composition, of an auxiliary fragrance material comprising amyl cinnamal, benzyl alcohol, cinnamyl alcohol, citral, eugenol, hydroxy-citronellal, isoeugenol, amylcin-namyl alcohol, benzyl-salicylate, cinnamal, coumarin, geraniol, hydroxy-methylpentylcyclohexanecarboxaldehyde, anisyl alcohol, benzyl cinnamate, farnesol, 2(4-tert-butylbenzylpropionaldehyde), linalool, benzyl benzoate, citronellol, hexyl cinnam-aldehyde, limonene, methyl heptin carbonate, 3-methyl-4-(2,6,6-tri-methyl-2-cyclohexen-1-yl)-3-buten-2-one, or combinations thereof.

20. The dispensing applicator according to claim 18, wherein the composition (14) is a topical aromatic releasing ointment, wherein the composition (14) comprises turpentine.

21. The dispensing applicator (2) according to claim 18, wherein at least a portion of the plurality of dispensing orifices (30) are spaced apart about the center axis (100).

* * * * *